United States Patent
Ishiguro et al.

(10) Patent No.: US 7,049,103 B2
(45) Date of Patent: May 23, 2006

(54) METHOD OF EVALUATING DRUG EFFICACY AND TOXICITY

(75) Inventors: Takahiko Ishiguro, Yokohama (JP); Kiyoshi Yasukawa, Kawasaki (JP); Shigeo Tsuchiya, Tokyo (JP)

(73) Assignee: Tosoh Corporation, Shinnanyo (JP)

( * ) Notice: Subject to any disclaimer, the term of this patent is extended or adjusted under 35 U.S.C. 154(b) by 354 days.

(21) Appl. No.: 10/266,605

(22) Filed: Oct. 9, 2002

(65) Prior Publication Data

US 2003/0108930 A1   Jun. 12, 2003

(30) Foreign Application Priority Data

Oct. 10, 2001   (JP) .............................. 2001-312716

(51) Int. Cl.
*C12P 19/34*   (2006.01)
*C12Q 1/68*   (2006.01)

(52) U.S. Cl. .................. 435/91.2; 435/91.1; 435/6

(58) Field of Classification Search .................. 436/6; 435/91.1, 91.2; 536/23.1, 24.33, 24.32, 25.32
See application file for complete search history.

(56) References Cited

U.S. PATENT DOCUMENTS

| 5,814,447 A | 9/1998 | Ishiguro et al. |
| 6,030,115 A | 2/2000 | Ishiguro et al. |
| 6,063,572 A | 5/2000 | Ishiguro et al. |
| 6,211,354 B1 | 4/2001 | Horie et al. |

FOREIGN PATENT DOCUMENTS

| EP | 0 534 640 | * | 3/1993 |
| EP | 0 969 101 | * | 1/2000 |
| WO | WO 97/13877 |   | 4/1997 |
| WO | WO 99/47709 | * | 9/1999 |

OTHER PUBLICATIONS

Burcynski et al. Drug Metabolism and Disposition. vol. 29, No. 9, pp. 1243-1250, Sep. 2001.*
Nakahara et al. Nucleic Acids Research, vol. 26, No. 7, pp. 1854-1855, Apr. 1998.*
Patent Abstracts of Japan, JP 11-000199, Jan. 6, 1999, Abstract only.
M. E. Burczynski, et al., Drug Metabolism and Disposition, vol. 29, No. 9, XP-002255571, pp. 1243-1250, "Cytochrome P450 Induction in Rat Hepatocytes Assessed by Quantitative Real-Time Reverse-Transcription Polymerase Chain Reaction and the RNA Invasive Cleavage Assay", Sep. 2001.
H. Myoung, et al., Cancer Letters, vol. 163, No. 2, XP-002255572, pp. 191-200, "Evaluation of the Anti-Tumor and Anti-Angiogenic Effect of Paclitaxel and Thalidomide on the Xenotransplanted Oral Squamous Cell Carcinoma", Feb. 26, 2001.

* cited by examiner

*Primary Examiner*—Kenneth R. Horlick
*Assistant Examiner*—Cynthia Wilder
(74) *Attorney, Agent, or Firm*—Oblon, Spivak, McClelland, Maier & Neustadt, P.C.

(57) ABSTRACT

A method of assaying the efficacy and/or toxicity of a test substance by expression of a specific gene in a cell or a microorganism, which comprises treating the cell or the microorganism with the test substance, a step of amplifying an RNA having a sequence homologous or complementary to a specific sequence in a target RNA obtained as the result of transcription of the specific gene, and a step of determining whether the target RNA is transcribed through the expression of the specific gene by detecting the RNA amplified in the previous amplification step.

6 Claims, 2 Drawing Sheets

METHOD OF EVALUATING DRUG EFFICACY AND TOXICITY

The present invention relates to a method of evaluating the efficacy and/or toxicity of a test substance through analysis of the expression of a specific gene in a cell or microorganism.

Exploratory research for drug development based on the cycle of molecular modeling, synthesis and efficacy evaluation seldom succeeds even with huge investments of time and money and therefore has a problem of how to improve efficiency. Computational chemistry has helped solving the problem by introducing theoretical molecular modeling based on the molecular structures of target proteins. Combinatorial synthesis also has greatly contributed to improvement in efficiency by facilitating synthesis of several to tens of thousands of compounds.

For evaluation of drug efficacy, so-called high throughput screening of large libraries of compounds for favorable functions through various bioactivity assays by automatic assay robots is commonly used. The diversity of bioactivity assays including from growth assay (halo assay) to enzyme assay and protein assay, is diverse, and it further increases, for example, if the conditions are varied in an enzyme assay according to the type of the enzyme. The great diversity is a hindrance to efficient exploratory research as well as to efficient toxicity tests for environmental assessments.

The advancement in gene amplification techniques such as PCR has made gene amplification common in fundamental studies. Genetic tests involving gene amplification are also widely used in the field of diagnosis of infectious diseases.

In bioactivity assays involving genetic tests, when a test substance shows efficacy, though considerable, in cells or microorganism by inhibiting the expression of a specific gene, namely by inhibiting the transcription of the specific gene into mRNA, not by degrading or eliminating the specific gene from the cells or microorganism, the expression product of the gene or mRNA, not the gene or DNA itself, should be measured as the measuring object which indicates the effect of the test substance on the cells or microorganism.

If this is the case, it follows that genetic tests using PCR, which gives DNA as the amplification product, are not suitable for evaluation of a test substance which inhibits the expression of the specific gene. Bioactivity assays which targets mRNA as the measuring object are theoretically possible if RT-PCR is applied to RNA extracts from cells or microorganisms if DNA is completely removed, but actually impractical in view of the complexity and difficulty of the extraction procedure. For studies in the field of molecular biology, northern blotting has been known as a method of specifically detecting mRNA. This method is cumbersome and has a lot of problems in its application in bioactivity assays for evaluation of drug efficacy in need of efficiency.

The object of the present invention is to provide a novel method of evaluating efficacy and/or toxicity of a test substance by analyzing the expression of a specific gene in cells or microorganisms by a genetic test.

The present invention has been accomplished to attain the above-mentioned object. The invention defined in claim 1 of the present application provides a method of assaying the efficacy and/or toxicity of a test substance by expression of a specific gene in a cell or a microorganism, which comprises treating the cell or the microorganism with the test substance, a step of amplifying an RNA having a sequence homologous or complementary to a specific sequence in a target RNA obtained as the result of transcription of the specific gene, and a step of determining whether the target RNA is transcribed through the expression of the specific gene by detecting the RNA amplified in the previous amplification step.

The invention defined in claim 2 of the present application provides the method according to claim 1, wherein the detection of the amplified RNA in the determining step is carried out by using an oligonucleotide probe labeled with a fluorescent intercalative dye which is capable of hybridizable to the RNA and by measuring the change in the fluorescence of the reaction solution. The invention defined in claim 3 of the present application provides the method according to claim 1 or 2, wherein the detection of the amplified RNA and the amplification of the target RNA are carried out at the same time. The invention defined in claim 4 of the present application provides the method according to claim 1, wherein the step of amplifying the target RNA comprises synthesizing a cDNA of the target RNA by the action of an RNA-dependent DNA polymerase, degrading the RNA strand in the resulting RNA•DNA hybrid by the action of rebonuclease H to leave a single-stranded DNA, forming a double-stranded DNA having a promoter sequence which can be transcribed into an RNA consisting of the specific base sequence or a sequence complementary to the specific base sequence by using the single-stranded DNA as a template by the action of a DNA-dependent DNA polymerase, and then transcribing the double-stranded DNA into an RNA transcript, which acts as a template in the subsequent cDNA synthesis by the RNA-dependent DNA polymerase, in the presence of an RNA polymerase, and the step of amplifying the target RNA uses first and second oligonucleotides consisting of at least 10 consecutive bases in the cDNA (either of which additionally has a promoter sequence for the RNA polymerase at the 5' end).

Figure 1:
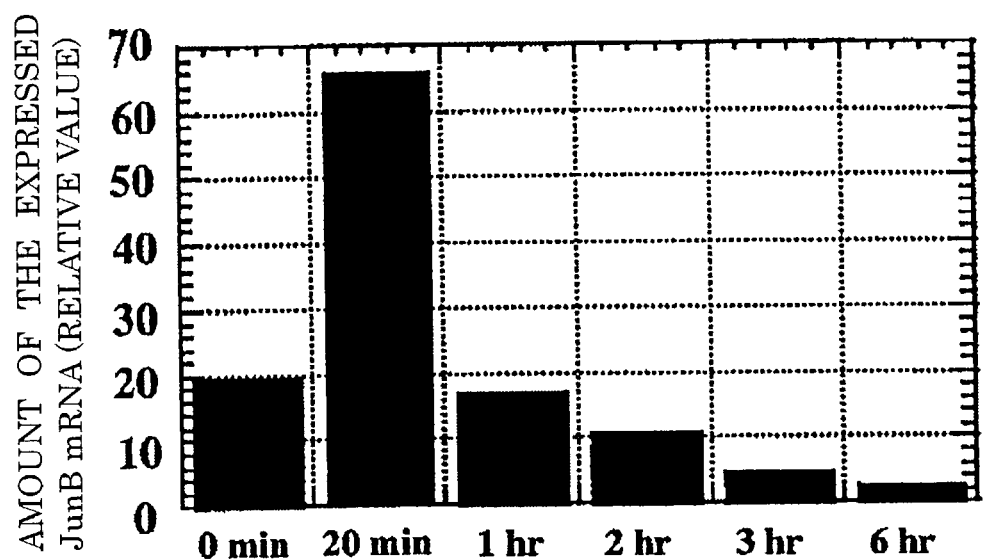
FIG. 1 shows the relative amount of the JunB mRNA expressed in human CD34+ cells after incubation for given periods in the presence of IL-6R•IL-6 fusion protein and SCF.

Now, the present invention will be described in detail.

In the present invention, what is amplified and detected is the mRNA (target RNA) transcribed in the course of the expression of a specific gene in a cell or a microorganism. The target RNA, or the mRNA to be amplified and detected, may be any mRNA that indicates the bioactivity of the cell or microorganism on which the drug efficacy or toxicity is evaluated, such as human JunB mRNA (an indicator of the differentiation of human CD34+ cells to haematopoietic precursor cells) mentioned in Examples and tubercle bacillus Pab mRNA (an indicator of the growth of tubercle bacillus) without any particular restrictions, but the target RNA of the present invention is not restricted to these specific examples.

In the present invention, treatment of cells or a microorganism with the test substance is followed by amplification of the target RNA (exactly speaking, an RNA sequence homologous or complementary to a specific sequence in the target RNA). Then, the amplified RNA is detected to show whether the target RNA is transcribed through the expression of the specific gene. The presence of the amplification product from the target RNA means successful transcription of the specific gene and therefore translates into lack of efficacy in the cells or microorganism (or proof for efficacy, if the test substance is desired to induce transcription of the specific gene). Conversely, the absence of the target RNA means that the specific gene was not transcribed and therefore translates into lack of efficacy in the cell or microorganism (proof for efficacy, if the test substance is desired to induce transcription of the specific gene). In any rate, it is preferred to carry out the same procedure by using a control RNA extracted from cells or a microorganism which has not been treated with the test substance.

The time period of treatment of a cell or a microorganism with a test substance may be arbitrarily set and is not particularly limited. However, when it is completely unpredictable how long it takes until the efficacy or toxicity is recognized, it is preferred, for example, to periodically sample the cells or the microorganism after the treatment and subject the samples to the evaluation method of the present invention so that it is possible to estimate the time necessary for recognition of efficacy or toxicity. There is no particular restriction on how to treat a cell or a microorganism with a test substance, and the test substance may be put into a culture of the cells or the microorganism or may be directly injected into the cells or the microorganism.

The treatment of the cells or the microorganism with the test substance is followed by extraction of nucleic acid from the cells or the microorganism. In the present invention, when the RNA-specific amplification step which will be mentioned later is employed, removal of DNA from the extracted nucleic acid is not necessary. For extraction of nucleic acid, the ordinary method commonly used may be used.

As mentioned above, though there is no particular restriction on the target RNA, mRNAs encoding proteins necessary for growth of the cell or the microorganism, such as RNA polymerase, catalase and DNA helicase, are suitable as the target RNA when the efficacy or toxicity of the test substance is evaluated from the effect against the growth of the cell or microorganism. Selection of an RNA unique to the cell or microorganism as the target RNA makes it possible to exclusively check the growth of the cell or microorganism even in the presence of other cells or microorganisms, and thereby makes it possible to evaluate whether the test substance shows efficacy or toxicity exclusively in the cell or microorganism, by just applying the method of the present invention to a target RNA in the specific cell or the like and to a target RNA in other cells. In contrast, the conventional growth assay based on cell counts under a microscope or the uptake of a dye or nucleic acid can not exclusively check the growth of a specific type of cells or microorganism in the presence of other types of cells or microorganisms.

When the efficacy or toxicity of a test substance on a specific defect or action of a cell or microorganism, a mRNA whose expression induces the defect or action is suitable as the target RNA. Such mRNAs include, for example, mRNAs encoding acute phase response proteins (such as haptoglobin) expressed in inflamed hepatic cells and a stress protein expressed in differentiating vascular smooth muscle cells.

The gene amplification method used in the amplification step in the present invention may be any RNA amplification method which allows a target RNA to be amplified specifically without any particular restriction, but is preferably an RNA amplification method which does not cause amplification of the specific gene (DNA) even in the presence of the specific gene. Especially, an RNA amplification method in which the entire procedure can be carried out isothermally, such as NASBA (Nucleic Acid Sequence Based Amplification; U.S. Pat. No. 2,650,159) and TMA (Transcription-Mediated Amplification, JP-A-4-500759), is preferred. In addition to these RNA amplification techniques, the method described later in the Examples (Japanese Patent Application JP10-186434, Japanese Unexamined Patent Publication JP-A-2000-14400) may be mentioned as an example. The amplification mechanism employed in all these RNA amplification methods is described below.

First, a first oligonucleotide complementary to a 3'-end sequence in the specific sequence in the target RNA is hybridized to the target RNA to direct an RNA-dependent DNA polymerase to synthesize the cDNA of the target RNA (exactly speaking, part of the target RNA including the specific sequence), which forms a hybrid with the target RNA (which has the first oligonucleotide at the 5' end of the DNA strand in it) in the reaction solution. The RNA strand in the RNA-DNA hybrid is degraded by ribonuclease H, leaving a single-stranded DNA.

A second oligonucleotide complementary to a 3'-end sequence in the resulting single-stranded DNA binds to the single-stranded DNA to direct a DNA-dependent DNA polymerase to synthesize a double-stranded DNA having a promoter sequence which can be transcribed into an RNA homologous or complementary to the specific sequence in the target RNA, by using the single-stranded DNA as the template. The resulting double-stranded DNA is transcribed into an RNA transcript homologous or complementary to the specific sequence in the target RNA in the presence of an RNA polymerase. The above-mentioned first oligonucleotide binds to the 3'-end of the resulting RNA transcript, which acts as the template for the subsequent cDNA synthesis by the RNA-dependent DNA polymerase.

For the synthesis of the double-stranded DNA having a promoter sequence to be transcribed into an RNA, either the first or second oligonucleotide has to have a promoter sequence for an RNA polymerase at the 5' end. In the present invention, the first and second oligonucleotides are preferably oligonucleotides containing at least 10 bases complementary to the target RNA or the single-stranded DNA. The respective oligonucleotides may be selected arbitrarily in consideration of the target RNA and the specific sequence in it.

As stated above, in the present invention, the target RNA can be amplified by NASBA, TMA or the method described in the Examples. The method described in the Examples makes it possible to carry out amplification of the target RNA and detection of the amplified RNA simultaneously within such a short time as from 10 to 15 minutes and therefore is particularly preferable to carry out the present invention.

The amplified RNA may be detected, for example, by electrophoresis or sandwich assay. Namely, since the length and sequence of the amplified RNA are known beforehand, amplification for a given period is followed by electrophoresis of the reaction solution and measurement of the density of the band of the RNA molecules with the known length, or by sandwich assay using an anchor nucleic acid probe and a labeled probe specific for the amplified RNA.

In the present invention, the use of such an oligonucleotide probe labeled with an fluorescent intercalative dye mentioned later in the Examples in the detection is particularly preferable. The oligonucleotide probe may, for example, be an oligonucleotide having a sequence complementary to the amplified RNA which has a fluorescent intercalative dye linked to a phosphorus atom in it via a linker. Such an oligonucleotide probe alters its fluorescence upon intercalation of the fluorescent intercalative dye to the double strand formed with a complementary nucleic acid (Ishiguro, T. et al., (1996) Nucleic Acids Res. 24 (24) 4992–4997, U.S. Pat. No. 3,189,000).

The sequence of the oligonucleotide in the oligonucleotide probe should contain a sequence complementary to at least part, preferably at least 10 consecutive bases in view of the specificity for the amplified RNA to be detected, of the amplified RNA. The part of the amplified RNA which is complementary to the oligonucleotide probe should not be complementary to the part of the amplified RNA which is complementary to the first or second oligonucleotide so that the binding of the oligonucleotide to the amplified RNA does not interfere with the binding of the first or the second oligonucleotide to the amplified RNA. In addition, when the amplification step is carried out in the presence of the oligonucleotide probe or when the oligonucleotide is added to a reaction solution without deactivation of the enzymes necessary for the amplification in the reaction solution (such as an RNA-dependent DNA polymerase), chemical modification such as addition of glycolic acid to the hydroxyl group at the 3' end of the probe is preferable so that the oligonucleotide probe does not elongate from the 3' end upon binding to the amplified RNA.

When the oligonucleotide probe is used in the detection, it is possible to add the oligonucleotide to the reaction solution after completion of the amplification of the target RNA and then measure the change in the fluorescence from the reaction solution. However, in the present invention, it is preferred to carry out the amplification step as described later in the Examples in the presence of the oligonucleotide probe in parallel with measurement of the change in the fluorescence from a reaction solution because the evaluation time is shorter than when amplification and detection are carried out separately. Further, when the amplification step is carried out preferably in the presence of an oligonucleotide probe, the oligonucleotide probe may be added to the reaction solution before or during the amplification of the target RNA, preferably before the amplification. Namely, it is particularly preferable to monitor the fluorescence from a reaction solution and measure the change in the fluorescence during the amplification step under temperature control (which maintains the temperature of the reaction solution constant as in NASBA, TMA and the RNA amplification described in the Examples), because it is possible to carry out the evaluation method of the present invention in one tube (without adding any reagents to the reaction solution in a tube afterward or sampling the reaction solution from the tube) at a constant temperature (without repeating heating and cooling as in PCR) in one step (by carrying out the entire procedure from the amplification to the detection without pretreatment of the target RNA or carrying out the amplification and the detection separately) and automate the evaluation method of the present invention more easily. For particularly preferable embodiments of the present invention, apparatuses such as those disclosed in Japanese Patent Application JP10-254913 (Japanese Unexamined Patent Publication JP-A-2000-88752) and in Japanese Patent Application JP11-18054 (Japanese Unexamined Patent Publication JP-A-2000-214090) are available.

Now, the present invention will be described in further detail by referring to Examples. However, the present invention is by no means restricted to these specific Examples.

EXAMPLE 1

Measurement of the Amount of JunB mRNA in CD34+ Cells from Human Cord Blood

Commercially available CD34+ cells from human cord blood (Bio Whittaker, Inc.) were lysed, suspended in a serum-free medium, Stem Span SFEM (Stem Cell, Inc.), and incubated for 1 hour with 5% $CO_2$ at 37° C. and a 100% humidity. The cells were collected by centrifugation, washed with PBS, suspended in a serum-free medium, Stem Span and dispensed into 14 mL tubes (Falcon, Inc.) in an amount of 51000 cells per tube and supplemented with 100 ng/mL cytokine Recombinant Rat SCF (AMGEN Ltd., hereinafter referred shortly as SCF), interleukin-6 receptor•interleukin-6 fusion protein (FP6) (Japanese Patent Application JP11-188650, Japanese Unexamined Patent Publication JP-A-2001-8690). No cytokine was added to control cultures.

The cultures were incubated at 37° C. and a 100% humidity with 5% $CO_2$ for 20 minutes, 1 hour, 2 hours, 3 hours and 6 hours and harvested by centrifugation (300 g ×5 minutes), and the total RNA was isolated using a commercial isolation kit (RNeasy Mini kit, Qiagen K.K.).

The RNA amplification step disclosed in Japanese Patent Application JP10-186434 (Japanese Unexamined Patent Publication JP-A-2000-144000) was followed using oligonucleotides of SEQ ID NOS:1 to 3 to amplify JunB mRNA transcribed from the junB gene in the RNA preparations. The oligonucleotide of SEQ ID NO:1 was used as a scissor oligonucleotide to cut JunB mRNA at the 5' end of a specific sequence and has an aminated hydroxyl group at the 3' end. The oligonucleotide of SEQ ID NO:2 as a first oligonucleotide contained a 5'-end sequence of the specific sequence and further had a promoter sequence for an RNA polymerase upstream of the 5'-end sequence of the specific sequence. The oligonucleotide of SEQ ID NO:3 as a second oligonucleotide was complementary to a 3'-end sequence of the specific sequence.

The amplification step was carried out in the presence of an oligonucleotide probe of SEQ ID NO:4 having a hydroxyl group modified with glycolic acid at the 3' end and a fluorescent intercalative dye linked to the phosphorus atom between T at the position 6 and T at the position 7 from the 5' end, so that the amplified RNA could be detected. The amounts of jumb mRNA in the RNA samples were read from a calibration curve obtained by using, as the standard RNA, junB-RNA obtained by in vitro transcription of a template double-stranded DNA having a base sequence in junB followed by isolation. The results are shown in FIG. 1.

The calibration curve was prepared by using 10 copies/5 μL to $10^7$ copies/5 μL dilutions of the standard RNA (448 mer) containing the bases 875–1322 of junB-RNA (numbered in accordance with Nucleic Acids Res. 18, 3047–3048, 1990) in an RNA diluent (10 mM Tris-HCl (pH 8.0), 1 mM EDTA, 0.5 U/μL RNase Inhibitor (Takara Shuzo, Co., Ltd.), 5 mM DTT).

For comparison, the efficacy of SCF, IL-6•IL-6R fusion protein in CD34+ cells from human cord blood was evaluated by a conventional evaluation method.

Two thousand and five hundred CD34+ cells from human cord blood (Bio Whittaker, Inc.) were dispensed with 1 mL of a serum-free medium, Stem Span SFEM (Stem Cell, Inc.)

containing 100 ng/mL SCF and 100 ng/mL IL-6•IL-6R fusion protein into each of 24 wells, and the suspension cultures were incubated at 37° C. and a 100% humidity with 5% $CO_2$. After 0, 3, 5, 7 and 10 days, 500 cells were dispensed in each 35 mm plastic suspension culture dish with 1 mL of α-MEM containing 40% methylcellulose, 30% FCS, 1% BSA, 0.01 mM 2-mercaptoethanol, SCF, TPO, EPO, IL-3, IL-6 and G-CSF and incubated in the semisolid cultures. Two weeks later, the colonies were identified through an inverted microscope. The colonies were classified as granulocyte colonies, macrophage colonies, granulocytes•macrophage colonies, blast cell colonies, erythroblast colonies and granulocyte•macrophage•erythroblast mixed colonies. Among the colonies, the blast cell colonies and the above-mentioned mixed colonies were counted, and the increase rates were calculated by dividing the colony count by that obtained without incubation in the serum-free medium and shown in FIG. 2.

Figure 2:
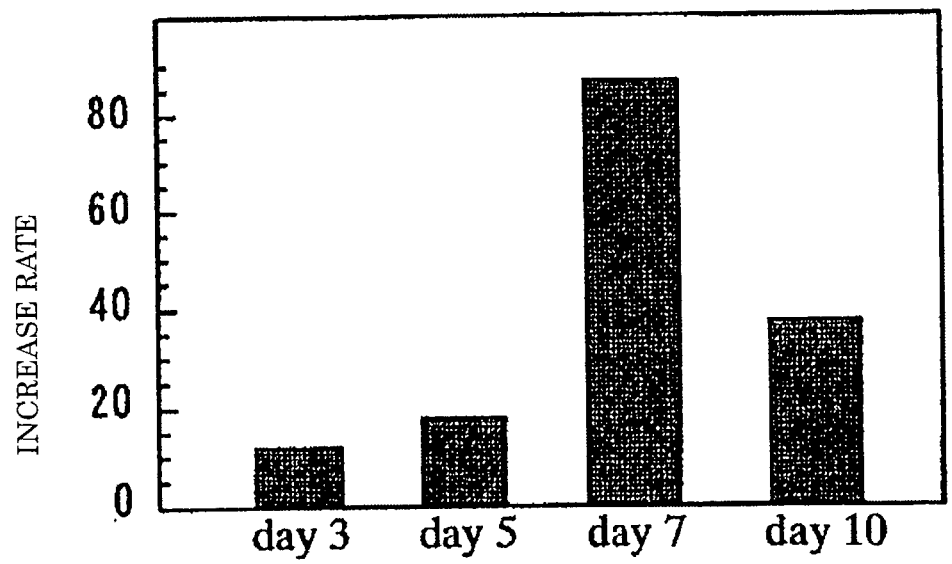
FIG. 2 shows the rate of the increase of colony-forming human CD34+ cells during given periods of incubations in the presence of IL-6R•IL-6 fusion protein and SCF.

FIG. 1 and FIG. 2 demonstrate agreement between the results obtained by the evaluation method of the present invention and the conventional evaluation method. Thus, the method of the present invention can finish tests which take several days when conducted by the conventional evaluation method involving incubation, in several hours.

EXAMPLE 2

Drug Sensitivity Test on BCG Strain

A BCG strain (obtained from the Murayama Branch of the National Institute of Infectious Diseases) was incubated in middlebrook 7H9 medium (DIFCO Laboratories) at 37° C. and a 100% humidity with 5% $CO_2$ to an OD of 0.1, diluted with the 7H9 medium by a factor of 100 and 10 mL of the dilution was poured into each of three 50 mL tubes. The BCG suspension in two tubes was supplemented with anti-tuberculous drugs, 40 μg/mL kanamycin and 2.5 μg/mL ethambutol, respectively, and the suspension in the remaining one was not supplemented and used as a control.

The BCG suspension cultures in the tubes were incubated at 37° C. and a 100% humidity with 5% $CO_2$, and 1 mL samples were withdrawn after 0, 3, 6, 9 and 24 hours and cryopreserved in liquid nitrogen.

The cryopreserved samples were thawed, and 250 μL portions of the samples were centrifuged in 1.5 mL tubes (15000 rpm, 3 minutes). The supernatants were removed, and the resulting pellets were suspended in 250 μL of an RNA diluent, and the tubes were vortexed with glass beads (Size 150–212, Sigma) in them for 5 minutes. The supernatants were poured into new 1.5 mL tubes, nucleic acid was extracted with EXTRAGEN (nucleic acid extraction kit, Tosoh Corporation), and the resulting pellets were suspended in 100 μL of an RNA diluent and used as test samples.

The mRNA of the tubercle bacillus pab gene in 5 μL of each of the samples thus obtained was amplified by the RNA amplification procedure disclosed in Japanese Patent Application JP10-186434 (Japanese Unexamined Patent Publication JP-A-2000-14400) by using the oligonucleotides of SEQ ID NOS:5 to 7. The oligonucleotide of SEQ ID NO:5 was used as a scissor oligonucleotide to cut the RNA derived from the pab gene at the 5' end of a specific sequence and had an aminated hydroxyl group at the 3' end. The oligonucleotide of SEQ ID NO:6 was used as a first oligonucleotide having a sequence homologous to a 5'-end sequence of the specific sequence and also had the promoter sequence for an RNA polymerase upstream of the homologous sequence. The oligonucleotide of SEQ ID NO:7 was used as a second oligonucleotide having a sequence complementary to a 3'-end sequence of the specific sequence.

The above-mentioned amplification step was carried out in the presence of an oligonucleotide probe of SEQ ID NO:8 which had a hydroxyl group modified with glycolic acid at the 3' end and had a fluorescent intercalative dye linked to the phosphorus atom between T at the position 10 and T at the position 11 from the 5' end.

For comparison, PCR was carried out using the same samples to amplify the 1326 bases from the position 111 to the position 1436 in the tubercle bacillus pab gene (numbered in accordance with inf. And immune., 57, 2481–2488, 1989). 75 μL of a reaction solution having the following composition was dispensed into 0.5 mL PCR tubes (Gene Amp Thin-Walled Reaction Tubes, Perkin Elmer), and 5 μL of the RNA samples were added. The composition of the reaction solution (in terms of the final concentrations in the final volume of 75 μL) was as follows.

10×LA PCR Buffer II 2.25 U TaKaRa LA Taq 2.2 mM $MgCl_2$ 0.25 mM each of dATP, dCTP, dGTP and dTTP 0.24 μM Primer MPCAL-F1 (bases 111 to 130, SEQ ID NO:9)

0.24 μM Primer MPCAL-R2 (bases 1427 to 1436, SEQ ID NO:10)

Distilled Water for Volume Adjustment

Then, the reaction solutions were incubated at 95° C. for 2 hours, and a cycle of 30-second incubation at 95° C., 30-second incubation at 55° C. and 3-minute incubation at 72° C. was repeated 30 times and followed by incubation at 72° C. for 10 minutes.

Figure 4:
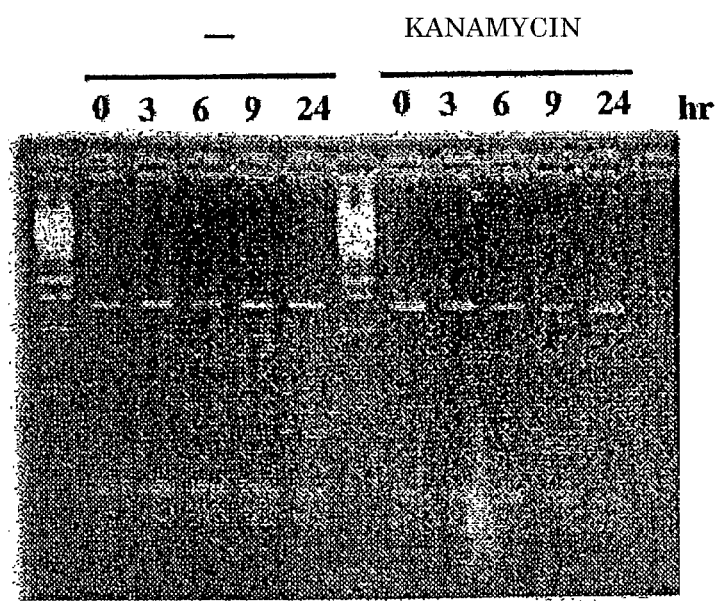
FIG. 4 shows an electrophoregram of the PCR amplification product of the Pab gene in nucleic acid extracts from a BCG strain incubated for 0, 3, 6, 9 and 24 hours in the absence of antibiotics in the presence of kanamycin.

The DNA amplified by the PCR was identified by agarose gel electrophoresis (agarose concentration 1.5%) followed by staining with ethidium bromide. The electrophoregram is shown in FIG. 4. The band containing the amplification product indicates that the amplified sequence was 1326 bases long. All the samples formed bands containing the specific sequence.

Figure 3:
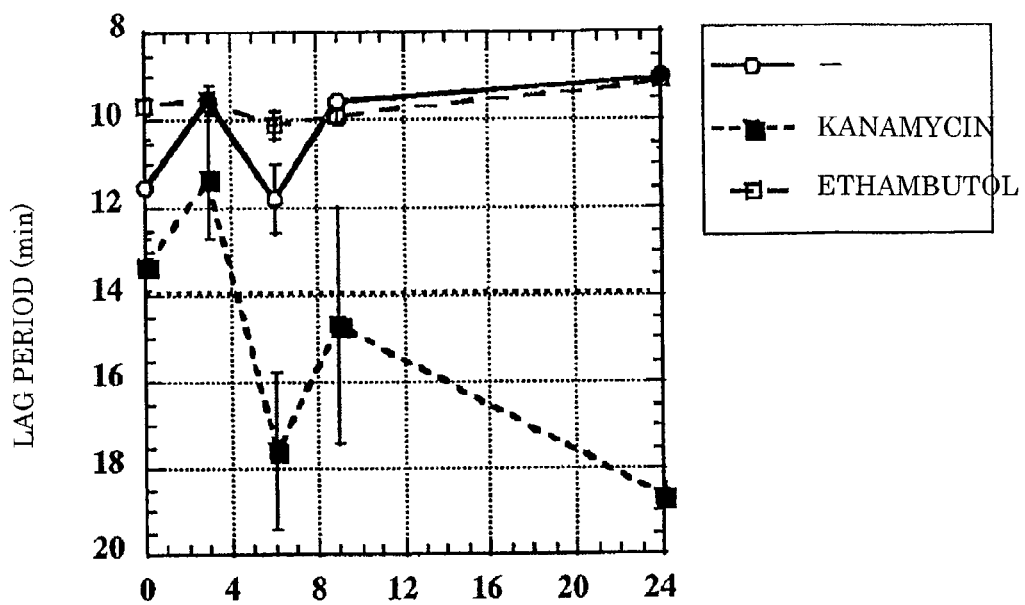
FIG. 3 shows the lag periods before amplification of Pab mRNA in nucleic acid extracts from a BCG strain incubated for 0, 3, 6, 9 and 24 hours in the absence of antibiotics and in the presence of kanamycin or ethambutol.

FIG. 3 and FIG. 4 demonstrate that the evaluation method of the present invention makes it possible to evaluate the efficacy of test substances which can not be detected by methods involving DNA amplification. Likewise, the method of the present invention makes it possible to evaluate the toxicity, which can not be evaluated by conventional methods involving DNA amplification, in a short time.

The method of evaluating drug efficacy and toxicity of the present invention based on the detection of gene expression meets various purposes of evaluation of drug efficacy and toxicity without using diverse bioactivity assays. It makes it possible to improve the efficiency of screening of drug candidates and drastically promote exploratory research and safety tests for drug development and is expected to greatly contribute to development of new therapeutic drugs. Further, in the field of environmental assessment, great numbers of test substances can be analyzed efficiently.

The entire disclosure of Japanese Patent Application No. 2001-312716 filed on Oct. 10, 2001 including specification, claims, drawings and summary is incorporated herein by reference in its entirety.

The invention claimed is:

1. A method of assaying the efficacy and/or toxicity of a test substance by expression of a specific gene in a cell or a microorganism, which comprises:

(a) treating the cell or the microorganism with the test substance, (b) extracting nucleic acids from the cell or the microorganism to provide a reaction solution, (c) amplifying, from said reaction solution containing nucleic acids, a target RNA having a sequence homologous or complementary to a specific sequence in a target mRNA in the reaction solution which is obtained by said extracting by a method comprising, synthesizing a cDNA of the target RNA with an RNA-dependent DNA polymerase, degrading the RNA strand in the resulting RNA•DNA hydrid with ribonuclease H to leave a single-stranded DNA, forming a double-stranded DNA having a promoter sequence which can be transcribed into an RNA comprising the specific base sequence or a sequence complementary to the specific base sequence by using the single-stranded DNA as a template for a DNA-dependent DNA polymerase, transcribing the double-stranded DNA into an RNA transcript, synthesizing a cDNA from the RNA transcript as a template by catalysis of an RNA-dependent DNA polymerase, and amplifying the target RNA with a first oligonucleotide and a second oligonucleotide consisting of at least 10 consecutive bases in the cDNA, (d) determining whether the target mRNA is transcribed through the expression of the specific gene by detecting the RNA amplified by said amplifying, and (e) assessing the efficacy and/or toxicity of said test substance by expression of the specific gene compared to expression of said the specific gene when in the absence of said test substance, wherein (c) and (d) are performed simultaneously.

2. The method according to claim 1, wherein said detecting comprises adding to the reaction solution an oligonucleotide probe labeled with a fluorescent intercalative dye which hybridizes to the amplified RNA and measuring the change in the fluorescence of the reaction solution.

3. The method according to claim 1, wherein either said first oligonucleotide or said second oligonucleotide has a promoter sequence for an RNA polymerase at the 5' end.

4. The method according to claim 1, wherein expression of the specific gene encodes an acute phase response protein expressed in inflamed hepatic cells.

5. The method according to claim 1, wherein expression of the specific gene encodes a stress protein expressed in differentiating vascular smooth muscle cells.

6. The method according to claim 1, wherein said amplifying is performed isothermally.

* * * * *

SEQUENCE LISTING

<160> NUMBER OF SEQ ID NOS: 10

<210> SEQ ID NO 1
<211> LENGTH: 35
<212> TYPE: DNA
<213> ORGANISM: ARTIFICIAL SEQUENCE
<220> FEATURE:
<223> OTHER INFORMATION: SYNTHETIC DNA

<400> SEQUENCE: 1
gggtacgagc tcccggtcgc gacggcagcc ccggc                          35

<210> SEQ ID NO 2
<211> LENGTH: 53
<212> TYPE: DNA
<213> ORGANISM: ARTIFICIAL SEQUENCE
<220> FEATURE:
<223> OTHER INFORMATION: SYNTHETIC DNA

<400> SEQUENCE: 2
aattctaata cgactcacta tagggagata cccgacgacc accatcagct acc       53

<210> SEQ ID NO 3
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 3
tgatgcgctc ttggtcttcc                                           20

<210> SEQ ID NO 4
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 4
tgcggttcct ccttgaaggt                                           20

<210> SEQ ID NO 5
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 5
tattgcctag ttgggcctcg ccga                                      24

<210> SEQ ID NO 6
<211> LENGTH: 51
<212> TYPE: DNA
<213> ORGANISM: ARTIFICIAL SEQUENCE
<220> FEATURE:
<223> OTHER INFORMATION: SYNTHETIC DNA

<400> SEQUENCE: 6
aattctaata cgactcacta tagggagata ggcaatagct ctggcaattt c         51

<210> SEQ ID NO 7
<211> LENGTH: 21

-continued

```
<212> TYPE: DNA
<213> ORGANISM: ARTIFICIAL SEQUENCE
<220> FEATURE:
<223> OTHER INFORMATION: SYNTHETIC DNA

<400> SEQUENCE: 7
cttttgccgg ttgttgacga t                                              21

<210> SEQ ID NO 8
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 8
tcgtagttga tgatcgggta                                                20

<210> SEQ ID NO 9
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 9
gacgccaagc gcggaaattg                                                20

<210> SEQ ID NO 10
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 10
agcaccaaca ccagcgcaag                                                20
```